United States Patent [19]
Easley

[11] Patent Number: 5,351,168
[45] Date of Patent: Sep. 27, 1994

[54] ILLUMINATION DEVICE FOR SURGERY

[75] Inventor: James C. Easley, St. Charles, Mo.

[73] Assignee: Infinitech, Inc., Chesterfield, Mo.

[21] Appl. No.: 49,092

[22] Filed: Apr. 16, 1993

[51] Int. Cl.$^5$ .......................... F21V 5/04; F21V 8/00; B24B 1/00

[52] U.S. Cl. ................................. 362/32; 362/109; 362/335; 65/61; 385/33; 606/17; 451/41

[58] Field of Search ................. 385/33, 117, 119, 147, 385/901; 606/17; 362/32, 109, 332, 335, 338, 119; 51/124 L, 283 R; 65/61

[56] References Cited

U.S. PATENT DOCUMENTS

| | | | |
|---|---|---|---|
| 3,131,690 | 5/1964 | Innis et al. | 362/32 |
| 3,439,157 | 4/1969 | Myles | 362/32 |
| 3,910,677 | 10/1975 | Becker et al. | 385/33 |
| 3,932,022 | 1/1976 | Henning et al. | 385/117 |
| 3,981,709 | 9/1976 | Kondo et al. | 65/61 |
| 4,641,912 | 2/1987 | Goldenberg | 606/17 |
| 4,678,268 | 7/1987 | Russo et al. | 385/33 |
| 4,693,244 | 9/1987 | Daikuzono | 606/17 |
| 4,693,556 | 9/1987 | McCaughan, Jr. | 385/147 |
| 4,733,933 | 3/1988 | Pikulski | 385/12 |
| 4,842,390 | 6/1989 | Sottini et al. | 606/17 |
| 4,995,691 | 2/1991 | Purcell, Jr. | 606/17 |
| 5,037,174 | 8/1991 | Thompson | 385/33 |

FOREIGN PATENT DOCUMENTS

| | | | |
|---|---|---|---|
| 139705 | 8/1982 | Japan | 385/901 |
| 248017 | 11/1986 | Japan | 385/117 |

*Primary Examiner*—Ira S. Lazarus
*Assistant Examiner*—Alan B. Cariaso
*Attorney, Agent, or Firm*—Polster, Lieder, Woodruff & Lucchesi

[57] ABSTRACT

An illumination device for use in surgery on the human body has a optical fiber which terminates distally in a bullet-shaped tip. The tip has an exterior surface which is a surface of revolution of a predetermined curve about the longitudinal axis of the tip, the predetermined curve having a first proximal segment, a second intermediate segment, and a third distal segment. The first segment has tangents substantially all of which make less than a first predetermined angle with the longitudinal axis. The second segment has tangents substantially all of which make angles with the longitudinal axis which are greater than the first predetermined angle and less than a second predetermined angle. The third segment has tangents substantially all of which make angles with the longitudinal axis which are greater than the second predetermined angle. A method of manufacturing the tip is disclosed as well.

15 Claims, 1 Drawing Sheet

ILLUMINATION DEVICE FOR SURGERY

BACKGROUND OF THE INVENTION

The present invention relates to illumination devices for use in surgery on the human body and more particularly to such devices especially suited for use in ophthalmic surgery and the like.

It is known that ophthalmic surgery (and other types of surgery such as laparoscopic and orthroscopic surgery) as well as various procedures such as endoscopy typically require an illumination probe or device which provides illumination for the area under treatment. To provide the best possible visualization for the physician/user of the device, it is preferred that the output of the illumination device be broadband (simulating sunlight to some degree), that the device itself be rather small (so as to not interfere with other instruments being used in the procedure, for example), that the device illuminate a relatively large area at one time, and that the light output over the illuminated area be fairly uniform (eliminating dark spots, excessively bright spots, etc.).

Often the illumination is transmitted from an illumination source (disposed at some distance from the patient) through an optical fiber cable to a handpiece which is manipulated by the physician/user or an assistant to provide illuminating light on the desired area.

Optical fiber cables do a good job of providing broad spectrum light from a suitable illumination source, but the light output of optical fibers could be improved. For example, the numerical aperture of optical fibers are typically rather small, with the result that the field of illumination for these devices is smaller than could be desired. Moreover, these devices are most often used in liquids (saline solutions and the like) which further reduces the field of illumination. Lenses have been used to spread the light from optical fibers, but these heretofore have resulted in uneven illumination (dark spots, bright spots, light rings, dark rings, etc.). At least one device (manufactured by Trek Medical) has been proposed to spread the light by changing the distal configuration of the optical fiber itself from the standard blunt shape. This Trek Medical device is believed to have included a cone formed into the distal end of the optical fiber with the tip of the cone forming the distal end of the fiber. This device also resulted in uneven light distribution.

SUMMARY OF THE INVENTION

Among the several objects and features of the present invention may be noted the provision of an improved illumination device which is especially suited for ophthalmic, laparoscopic, or orthroscopic surgery and endoscopy or the like.

Another object is the provision of such an illumination device which provides an improved field of illumination, even when used in liquids.

A third object is the provision of such an illumination device which provides even illumination over the field of illumination.

A fourth object is the provision of such an illumination device which is reliable, yet relatively simple to manufacture.

Other objects and features will be in part apparent and in part pointed out hereinafter.

Briefly, an illumination device for use in surgery on the human body includes a handpiece adapted to allow manipulation thereof by a user, a light source connector adapted for connection to a light source, and a hollow probe extending from a distal end of the handpiece and fixedly connected thereto. The probe is sized to fit within one or more cavities in the human body. At least one optical fiber extends from the light source connector to the probe for transmitting illuminating light from the light source through the probe. The device also includes a tip optically connected to the optical fiber, the tip being disposed at the distal end of the optical fiber and having an exterior surface which is a surface of revolution of a predetermined curve about the longitudinal axis of the tip. The predetermined curve has a first proximal segment, a second intermediate segment, and a third distal segment. The first segment has tangents substantially all of which make less than a first predetermined angle with the longitudinal axis. The second segment has tangents substantially all of which make angles with the longitudinal axis which are greater than the first predetermined angle and less than a second predetermined angle. The third segment has tangents substantially all of which make angles with the longitudinal axis which are greater than the second predetermined angle.

A method of the present invention is directed to making a tip for a optical fiber for use in surgery on the human body. The method includes polishing an end of an optical fiber to approximate a desired shape, disposing the polished end of the optical fiber under water and shining illuminating light from a light source through the optical fiber to generate an illumination pattern under water, comparing the illumination pattern under water with a desired illumination pattern, and polishing selected portions of the polished end of the optical fiber to correct any variations between the generated illumination pattern under water and the desired illumination pattern.

BRIEF DESCRIPTION OF THE DRAWINGS

Similar reference characters indicate similar parts throughout the several views of the drawings.

DESCRIPTION OF THE PREFERRED EMBODIMENT

Figure 1:
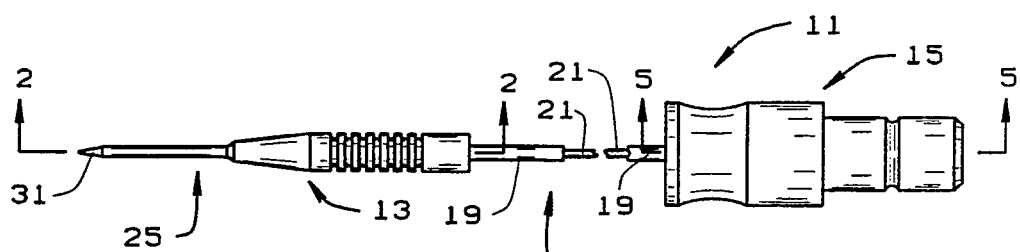
FIG. 1 is is a side elevation of the illumination device of the present invention.

Turning to the drawings, an illumination device 11 of the present invention includes a handpiece 13, an illumination light source connector 15, and an optical fiber cable 17. Optical fiber cable 17 typically includes a protective sheath 19 covering either a single or multiple optical fibers 21. A single plastic fiber having a numerical aperture of 0.5 in air is preferred, although multiple fibers or glass fibers could also be used in the present invention.

A hollow metal probe 25 is connected to handpiece 13 and extends distally therefrom. Handpiece 13 is used to manipulate the position of probe 25 to provide illumination passing through the probe to the desired locations during an operation or procedure. For ophthalmic surgery, probe 25 is of a size suitable for insertion into a human eye. Illumination devices for other operations and procedures could differ in size.

Although illumination device 11 is described herein solely as providing illumination, it should be understood that various other features could be added thereto. For example, a pic, an irrigation/aspiration lumen, a laser capability, and various other features could be added as desired.

As can be readily seen in FIG. 1, optical fiber cable 17 terminates proximally in illumination connector 15 in such a manner that it is exposed to illuminating light from the light source. The optical cable extends for any desired length (such an eight feet or so) and terminates distally adjacent probe 25. Optical fiber cable 17 thereby forms an optical path for the illuminating light from the light source to an eye (or other body part or organ).

Figure 2:
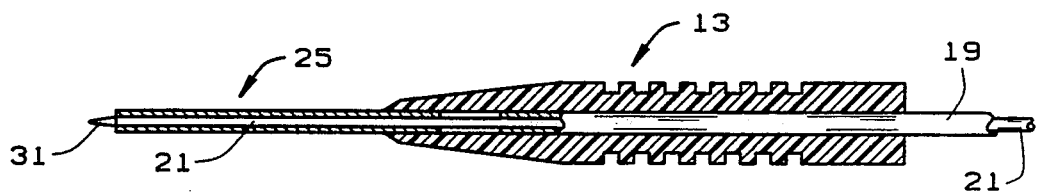
FIG. 2 is an enlarged sectional view taken along lines 2—2 of FIG. 1.

As can be seen more clearly in FIG. 2, sheath 19 terminates in handpiece 13 while the optical fiber 21 itself terminates at the distal end of the probe in a bullet-shaped tip 31. Although tip 31 is preferably formed on the distal end of optical fiber 21 as described below, it may also be formed as a separate part which is suitably secured to the distal end of probe 25. Tip 31 is shaped so as to provide uniform illumination over as wide a field of illumination as possible when the tip is disposed under water or some similar liquid.

It has been discovered that a shape for tip 31 which provides even illumination in air is less than satisfactory when used in water (typically a saline solution). This is apparently due to the great difference in the refractive indices of air and water. The present tip is specifically designed for use in water or a similar liquid since many operations, particularly ophthalmic procedures, are performed under those conditions. It has been found that this shape also functions fairly well in air, although not as well as a shape which is optimized for those conditions.

Figure 3:
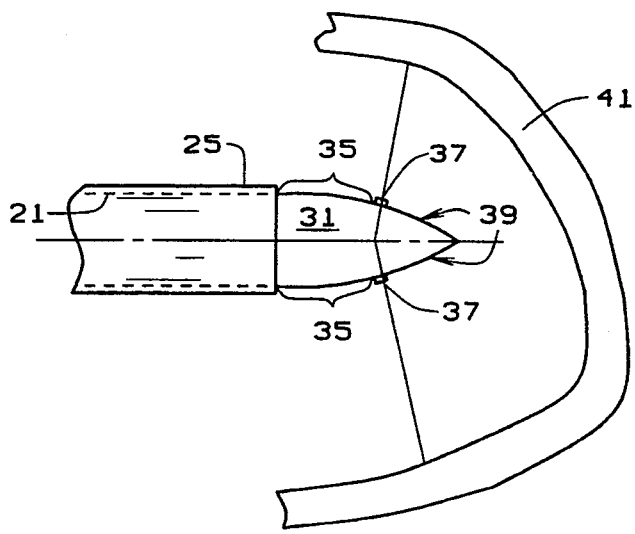
FIG. 3 is a an enlarged side elevation of the distal tip of the illumination device of FIG. 1 in use.
Figure 4:
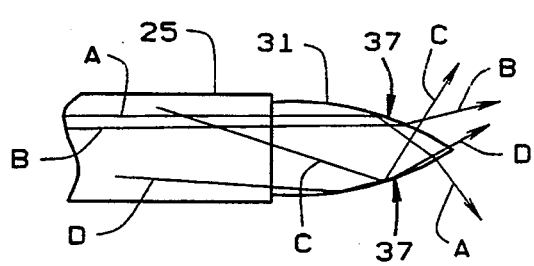
FIG. 4 is a view similar to FIG. 3 illustrating how the device functions in part.

Specifically referring to FIGS. 3 and 4, bullet-shaped tip 31 is optically connected to optical fiber 21 and preferably is an integrally formed part of the optical fiber. Tip 31 forms the distal end of the optical fiber and has an index of refraction of 1.49 or so. The particular values of index of refraction and numerical aperture herein are for purposes of illustration only, since they will vary depending upon the particular optical fiber being used. It should be appreciated that water (and saline solution) has an index of refraction of 1.33 or so, while air has a refractive index of 1.0.

Tip 31 is shaped to provide even illumination (within twenty per cent or so) over as wide a field as possible in water. A field of illumination of 150 degrees is achievable with the present design and is illustrated in FIG. 3. These goals are achieved in the shape shown in FIGS. 3 and 4 in which the shape of the tip progressively changes as the distal end of the tip is approached. The exterior surface of tip 31 can be divided into three zones 35, 37 and 39. In zone 35 the curvature of the tip is so slight that substantially all the light passing down optical fiber 21 is internally reflected since all possible angles of incidence are less than the critical angle for the tip in water. For the tip material described above, the critical angle is about 63 degrees. Immediately distal of zone 35 is intermediate transition zone 37. In this zone, which is relatively short, total internal reflection stops and some light begins to exit from tip 31. This occurs because the angle of incidence of some light rays in the transition zone exceed the critical angle and those rays are refracted out into the surrounding water.

Zone 39, the remainder of tip 31 distal from zone 37, is the area in which the light exits substantially uniformly from the tip to illuminate the desired portion (labelled 41) of the human body. Although the tip of zone 39 is shown as pointed, in fact it is slightly rounded to provide uniform illumination.

More particularly, tip 31 has an exterior surface which is a surface of revolution of a predetermined curve about the longitudinal axis of the tip. The predetermined curve includes a first proximal segment which generates reflection zone 35, a second intermediate segment which generates transition zone 37, and a third distal segment which generates zone 39. It should be appreciated that the light in zone 39 is both refracted out of the tip and reflected inside the tip, depending upon the actual angle of incidence of the particular ray. The first segment of the generating curve has tangents substantially all of which make less than a first predetermined angle with the longitudinal axis. This angle is chosen depending upon the material making up the fiber to ensure that substantially all possible light from optical fiber 21 is internally reflected in zone 35. The second, transition zone generating segment has tangents substantially all of which make angles with the longitudinal axis which are greater than the first predetermined angle and less than a second predetermined angle. These angles are selected to ensure that total internal reflection ceases in the transition zone. The third segment has tangents substantially all of which make angles with the longitudinal axis which are greater than the second predetermined angle so that in the third zone substantial amounts of light are refracted out of tip 31.

It is preferred that the generating curve be a smooth, continuous curve since it has been found that this leads to a more uniform illumination level across the field. Abrupt transitions tend to cause light areas and dark areas by focusing the light preferentially to particular areas. It can also be seen from FIG. 3 that the radii of curvature in the total internal reflection zone, zone 35, are greater than those in zone 37, and that the radii of curvature in zone 37 are greater than those in zone 39. It is preferred that the radii of curvature decrease from proximal end to the distal end of each segment as well so that the angle the tangent to exterior surface of the tip makes with the longitudinal axis of the tip substantially continuously varies from the proximal end of the tip to the distal end of the tip. This provides a complex shape which provides even illumination over a wide field in water.

It is well-known that optical fibers such as fiber 21 include a core and a thin cladding layer. In the area of tip 31, the cladding layer is removed so that the optical properties of the tip are not influenced by the cladding, which has a somewhat different index of refraction.

With this construction, tip 31 in water has a numerical aperture in degrees at least twice the numerical aperture of the optical fiber 21 in water.

Turning to FIG. 4, four light rays A, B, C, and D are shown to illustrate some of the characteristics of tip 31. For clarity only transition zone 37 is labelled. Ray A is roughly parallel to the longitudinal axis of tip 31 and strikes the surface proximally of the transition zone. Because this is an area of total internal reflection, the ray is reflected toward the distal end of the tip where it strikes the surface and is refracted out. Ray B is parallel to ray A but initially strikes the surface of tip 31 distally of the transition zone and is immediately refracted out of the tip. Ray C, like ray A, strikes the surface proximally of the transition zone 37 and is totally internally reflected, even though ray C is incident at a much higher angle than ray A. After reflection, ray C strikes the surface distally of zone 37 and is refracted out. Ray D undergoes multiple internal reflections before finally exiting tip 31. It should be appreciated that although ray D is shown exiting near the distal end of the tip, in fact rays which undergo multiple internal reflections may exit the tip at relatively high angles with respect to the axis.

It has been found that tip 31 is relatively easy to make. First, the end of optical fiber 21 is polished (which removes the cladding) in such a manner to approximate the desired bullet shape. The tip is then placed in water and the optical fiber tested by shining light therethrough. This generates an illumination pattern under water, which it has been found differs drastically from the illumination pattern for the same tip shape in air. The illumination pattern is visually compared with the desired uniform illumination pattern. If the generated illumination pattern has excessively bright areas or dark areas, the tip is polished selectively in such a manner as to remove the bright or dark areas and make the illumination under water uniform. It has been found that different generated illumination patterns represent different defects in shape. For example, a dark ring disposed around a bright spot indicates that the radii of curvature in zone 39 are too small, while a bright ring disposed around a darker central spot means that radii in zone 39 are too large. By polishing selected portions of the polished end of the optical fiber as indicated by the generated pattern, any variations in tip shape from the desired shape may readily be corrected.

Figure 5:
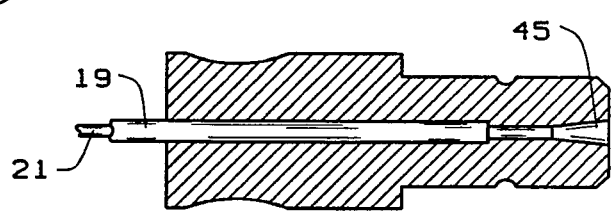
FIG. 5 is a partial elevation of the proximal portion of the illumination device of FIG. 1, on an enlarged scale.

Turning to FIG. 5, light source connector 15 is shown in more detail. Of special note is the bell-shape 45 of the proximal end of connector 15 which is used to funnel light from the light source into optical fiber 21.

In view of the above it will be seen that the various objects and features of the above described invention are achieved and other advantageous results obtained. The description and drawings of the present invention contained herein are illustrative only and are not to be interpreted in a limiting sense.

What is claimed is:

1. In an illumination device for use in surgery on the human body, said illumination device including a handpiece adapted to allow manipulation thereof by a user, a light source connector adapted for connection to a broadband light source, a hollow probe extending from a distal end of the handpiece and fixedly connected thereto, said probe being sized to fit within one or more cavities in the human body, and at least one optical fiber extending from the light source connector to the probe for transmitting broadband illuminating light from the light source through the probe, the improvement comprising:

an exposed tip optically connected to the optical fiber, said tip being disposed at the distal end of the optical fiber, said tip having an exterior surface which is a surface of revolution of a predetermined curve about the longitudinal axis of the tip, said predetermined curve having a first proximal segment, a second intermediate segment, and a third distal segment, the first segment having tangents substantially all of which make less than a first predetermined angle with the longitudinal axis, the second segment having tangents substantially all of which make angles with the longitudinal axis which are greater than the first predetermined angle and less than a second predetermined angle, and the third segment having tangents substantially all of which make angles with the longitudinal axis which are greater than the second predetermined angle, said predetermined curve having a plurality of radii of curvature, said exposed tip having a cross-sectional area which decreases substantially continuously distally from the distal end of the optical fiber.

2. The illumination device as set forth in claim 1 wherein the tip is integral with the optical fiber.

3. The illumination device as set forth in claim 1 wherein the tip is bullet shaped.

4. The illumination device as set forth in claim 1 wherein the tip is composed of unclad optical fiber.

5. The illumination device as set forth in claim 1 wherein the angle the tangent to exterior surface of the tip makes with the longitudinal axis of the tip substantially continuously varies from the proximal end of the tip to the distal end of the tip.

6. The illumination device as set forth in claim 1 wherein the first proximal segment defines a first portion of the tip in which light passing down the optical fiber is wholly internally reflected inside the tip.

7. The illumination device as set forth in claim 1 wherein the second intermediate segment defines a second portion of the tip in which some light passing down the optical fiber is refracted out of the tip.

8. The illumination device as set forth in claim 1 wherein the third distal segment defines a third portion of the tip in which a substantial fraction of the light passing down the optical fiber is refracted out of the tip.

9. The illumination device as set forth in claim 1 wherein the optical fiber has a predetermined numerical aperture in water and wherein the tip in water has a numerical aperture at least twice the numerical aperture of the optical fiber in water.

10. The illumination device as set forth in claim 1 wherein the exterior surface is shaped such that light exits from the tip over a predetermined angle measured with respect to a predetermined location along the longitudinal axis of the tip, the light exiting from the tip being substantially homogeneous over at least 120 degrees, measured with respect to said predetermined location, in water.

11. In an illumination device for use in surgery on the human body, said illumination device including a handpiece adapted to allow manipulation thereof by a user, a light source connector adapted for connection to a light source, a hollow probe extending from a distal end of the handpiece and fixedly connected thereto, said probe being sized to fit within one or more cavities in the human body, and at least one optical fiber extending from the light source connector to the probe for transmitting light from the light source through the probe, the improvement comprising:

an exposed tip optically connected to the optical fiber, said tip being disposed at the distal end of the optical fiber, said tip being substantially bullet shaped and having a cross-sectional area which decreases substantially continuously distally from the distal end of the optical fiber.

12. In an illumination device for use in surgery on the human body, said illumination device including a handpiece adapted to allow manipulation thereof by a user, a light source connector adapted for connection to a light source, a hollow probe extending from a distal end of the handpiece and fixedly connected thereto, said probe being sized to fit within one or more cavities in the human body, and at least one optical fiber extending from the light source connector to the probe for transmitting illuminating light from the light source through the probe, and improvement comprising:

a tip optically connected to the optical fiber, said tip being disposed at the distal end of the optical fiber, said tip having a shape such that light exits from the tip over a predetermined angle measured with respect to a predetermined location along the longitudinal axis of the tip, the light exiting from the tip being substantially homogeneous over at least 120 degrees, measured with respect to said predetermined location, in water.

13. A method of making a tip for a optical fiber for use in surgery on the human body comprising:

polishing an end of an optical fiber to approximate a desired shape;

disposing the polished end of the optical fiber under water and shining illuminating light from a light source through the optical fiber to generate an illumination pattern under water;

comparing the illumination pattern under water with a desired illumination pattern; and polishing selected portions of the polished end of the optical fiber to correct any variations between the generated illumination pattern under water and the desired illumination pattern.

14. The method as set forth in claim 13 wherein the desired illumination pattern is substantially homogeneous illumination over an illumination angle of at least 120 degrees.

15. The method as set forth in claim 13 wherein the desired shape is a bullet shape.

* * * * *